US012114628B2

(12) United States Patent
Shao et al.

(10) Patent No.: US 12,114,628 B2
(45) Date of Patent: Oct. 15, 2024

(54) INBRED RICE LINE DG263L

(71) Applicant: Nutrien AG Solutions, Inc., Loveland, CO (US)

(72) Inventors: Qiming Shao, Sugar Land, TX (US); Nanyen Chou, Sugar Land, TX (US); Kirk Douglas Johnson, Davis, CA (US)

(73) Assignee: Nutrien AG Solution, Inc., Loveland, CO (US)

( * ) Notice: Subject to any disclaimer, the term of this patent is extended or adjusted under 35 U.S.C. 154(b) by 234 days.

(21) Appl. No.: 17/729,926

(22) Filed: Apr. 26, 2022

(65) Prior Publication Data

US 2022/0386549 A1 Dec. 8, 2022

Related U.S. Application Data

(60) Provisional application No. 63/196,202, filed on Jun. 2, 2021.

(51) Int. Cl.
  *A01H 6/46* (2018.01)
  *A01H 5/10* (2018.01)

(52) U.S. Cl.
  CPC ............. *A01H 6/4636* (2018.05); *A01H 5/10* (2013.01)

(58) Field of Classification Search
  None
  See application file for complete search history.

(56) References Cited

U.S. PATENT DOCUMENTS

| | | |
|---|---|---|
| 3,710,511 A | 1/1973 | Patterson |
| 3,861,709 A | 1/1975 | Mulcahy et al. |
| 4,654,465 A | 3/1987 | Brar et al. |
| 4,727,219 A | 2/1988 | Brar et al. |
| 4,769,061 A | 9/1988 | Comai |
| 5,008,200 A | 4/1991 | Ranch et al. |
| 5,024,944 A | 6/1991 | Collins et al. |
| 5,432,068 A | 7/1995 | Albertsen et al. |
| 5,463,175 A | 10/1995 | Barry et al. |
| 5,591,616 A | 1/1997 | Hiei et al. |
| 5,639,948 A | 6/1997 | Michiels et al. |
| 5,776,760 A | 7/1998 | Barry et al. |
| 7,135,615 B2 | 11/2006 | Kato |
| 7,351,891 B2 * | 4/2008 | Sarreal ................. A01H 6/4636 800/278 |
| 7,462,481 B2 | 12/2008 | Castle et al. |
| 9,955,646 B1 | 5/2018 | Jodari et al. |
| 2004/0078852 A1 | 4/2004 | Thomashow et al. |
| 2004/0098764 A1 | 5/2004 | Heard et al. |

FOREIGN PATENT DOCUMENTS

| | | |
|---|---|---|
| WO | 92/13956 A1 | 8/1992 |
| WO | 92/13957 A1 | 8/1992 |
| WO | 96/30530 A1 | 10/1996 |
| WO | 99/25821 A1 | 5/1999 |
| WO | 01/29237 A2 | 4/2001 |

OTHER PUBLICATIONS

Ahn, et al., "Comparative linkage maps of the rice and maize genomes," Proceedings of the National Academy of Sciences of the U.S.A., vol. 90, Issue 17, Sep. 1, 1993 pp. 7980-7984.
Atanassova, et al., "A 126 bp fragment of a plant histone gene promoter confers preferential expression in meristems of transgenic Arabidopsis," The Plant Journal, vol. 2 Issue 3, May 1992, pp. 291-300.
Becker, et al., "Thecab-m7 gene: a light-inducible, mesophyll-specific gene of maize," Plant Molecular Biology, vol. 20, Oct. 1992, pp. 49-60.
Chalfie, et al., "Green Fluorescent Protein as a Marker for Gene Expression," Science, vol. 263, Issue 5148, Feb. 11, 1994, pp. 802-805.
Cheng, et al., "Toward a cytological characterization of the rice genome," Genome Research, vol. 11, Issue 12, Dec. 2001, pp. 2133-2141.
Christensen, et al., "Maize polyubiquitin genes: structure, thermal perturbation of expression and transcript splicing, and promoter activity following transfer to protoplasts by electroporation," Plant Molecular Biology, vol. 18, Feb. 1992, pp. 675-689.
Christensen, et al., "Sequence analysis and transcriptional regulation by heat shock of polyubiquitin transcripts from maize," Plant Molecular Biology, vol. 12, Jun. 1989, pp. 619-632.
Creissen, et al., "Molecular characterization of glutathione reductase cDNAs from pea (*Pisum sativum L.*)," The Plant Journal, vol. 2, Issue 1, Jan. 1992, pp. 129-131.
De Block, et al., "Expression of foreign genes in regenerated plants and in their progeny," The EMBO Journal, vol. 3, Issue 8, Aug. 1984, pp. 1681-1689.
Dinka et al., "Predicting the size of the progeny mapping population required to positionally clone a gene," Genetics, vol. 176, Issue 4, Aug. 2007, pp. 2035-2054.
Elzen, et al., "A chimaeric hygromycin resistance gene as a selectable marker in plant cells." Plant Molecular Biology, vol. 5, Sep. 1985, pp. 299-302.

(Continued)

*Primary Examiner* — Brent T Page
*Assistant Examiner* — Aleksandar Radosavljevic
(74) *Attorney, Agent, or Firm* — Faegre Drinker Biddle & Reath LLP

(57) ABSTRACT

The inbred rice line designated DG263L is disclosed. Embodiments include the seeds of inbred rice line designated DG263L, the plants of inbred rice line designated DG263L, plant parts of inbred rice line designated DG263L, and methods for producing a rice plant produced by crossing rice DG263L with itself or with another rice variety. Embodiments include methods for producing a rice plant containing in its genetic material one or more genes or transgenes and the transgenic rice plants and plant parts produced by those methods. Embodiments also relate to rice cultivars, breeding cultivars, plant parts, and cells derived from inbred rice line designated DG263L, methods for producing other rice cultivars, lines or plant parts derived from inbred rice line designated DG263L, and the rice plants, varieties, and their parts derived from use of those methods. Embodiments further include hybrid rice seeds, plants, and plant parts produced by crossing DG263L with another rice cultivar.

9 Claims, No Drawings

(56) References Cited

OTHER PUBLICATIONS

Fehr W., "Principles of cultivar development," Theory and technique, vol. 1, 1987, pp. 261-286.
Fontes, et al., "Characterization of an immunoglobulin binding protein homolog in the maize floury-2 endosperm mutant," The Plant Cell, vol. 3, Issue 5, May 1991, pp. 483-496.
Fraley, et al., "Expression of bacterial genes in plant cells," PNAS, vol. 80, No. 15, Aug. 1, 1983, pp. 4803-4807.
Gonzalez et al., "Molecular and Pathotypic Characterization of New Xanthomonas oryzae Strains from West Africa," Mol Plant Microbe Interact, vol. 20, No. 5, 2007, pp. 534-546.
Gould, et al., "A conserved tripeptide sorts proteins to peroxisomes," J Cell Biol, vol. 108, Issue 5, May 1, 1989, pp. 1657-1664.
Gruber et al., "Vectors for plant transformation," Methods in plant molecular biology and biotechnology, Glick and Thompson, Eds., 1993 pp. 89-119.
Guerrero, et al., "Promoter sequences from a maize pollen-specific gene direct tissue-specific transcription in tobacco," Molecular and General Genetics (MGG), vol. 224, Nov. 1990, pp. 161-168.
Hershey et al., "Regulation of a modified CaMV 35S promoter by the Tn10-encoded Tet repressor in transgenic tobacco," Molecular and General Genetics (MGG), vol. 227, Jun. 1991, pp. 229-237.
Horsch, et al., "A Simple and General Method for Transferring Genes into Plants," Science, vol. 227, Issue 4691, Mar. 8, 1985, pp. 1229-1231.
Huang et al. (2007), J. Genet. Genomics, 33(4):330-338.
Jefferson, et al., "Assaying chimeric genes in plants: The GUS gene fusion system," Plant Molecular Biology Reporter, vol. 5, Dec. 1987, pp. 387-405.
Jin, et al., "Molecular and cytogenetic characterization of an Oryza officinalis-O. sativa chromosome 4 addition line and its progenies, " Plant Molecular Biology, vol. 62, 2006, pp. 769-777.
Kado, et al., "Molecular mechanisms of crown gall tumorigenesis," Critical Reviews in Plant Sciences, vol. 10, No. 1, 1991, pp. 1-32.
Kalderon, et al. "A short amino acid sequence able to specify nuclear location," Cell, vol. 9, Issue 3, Part 2, Dec. 1984, pp. 499-509.
Kao, et al., "An integrated map of Oryza sativa L. chromosome 5," Theoretical and Applied Genetics, vol. 112, Issue 5, Mar. 2006, pp. 891-902.
Knox, et al., "Structure and organization of two divergent a-amylase genes from barley," Plant Molecular Biology, vol. 9, Janauary 1987, pp. 3-17.
Komatsuda, et al., "Genotype X Sucrose Interactions for Somatic Embryogenesis in Soybean," Crop Science, vol. 31, Issue 2, Apr. 1991, pp. 333-337.
Koncz, et al., "Expression and assembly of functional bacterial luciferase in plants," PNAS, vol. 84, Issue 1, Jan. 1, 1987, pp. 131-135.
Last, et al., "pEmu: an improved promoter for gene expression in cereal cells, " Theoretical and Applied Genetics, vol. 81, May 1991, pp. 581-588.
Lawson, et al., "Distinct patterns of SSR distribution in the Arabidopsis thaliana and rice genomes," Genome Biology, vol. 7, Article No., R14, Feb. 21, 2006.
Lepetit, et al., "A plant histone gene promoter can direct both replication-dependent and -independent gene expression in transgenic plants," Molecular and General Genetics (MGG), vol. 231, Jan. 1992, pp. 276-285.
Lerner, et al., "Cloning and Characterization of Root-Specific Barley Lectin," Plant Physiology, vol. 91, Issue 1, Sep. 1989, pp. 124-129.
Lu, et al., "Population Structure and Breeding Patterns of 145 U.S. Rice Cultivars Based on SSR Marker Analysis," Crop Science, vol. 45, Issue 1, Jan. 2005, pp. 66-76.
Luo, et al., "RTS, a rice anther-specific gene is required for male fertility and its promoter sequence directs tissue-specific gene expression in different plant species," Plant Molecular Biology, vol. 62, Aug. 1, 2006, pp. 397-408.
Lyznik, et al., "Site-specific recombination for genetic engineering in plants," Plant Cell Reports, vol. 21, Apr. 26, 2003, pp. 925-932.
Matsuoka, et al., "Propeptide of a precursor to a plant vacuolar protein required for vacuolar targeting," PNAS, vol. 88, Issue 3, Feb. 1, 1991, pp. 834-838.
Mcelroy, et al., "Isolation of an efficient actin promoter for use in rice transformation," The Plant Cell, vol. 2, Issue 2, Feb. 1990, pp. 163-171.
Mett et al., "Copper-controllable gene expression system for whole plants", PNAS, vol. 90, Issue 10, 1993, pp. 4567-4571.
Miki et al., "Procedures for Introducing Foreign DNA into Plants," Methods in Plant Molecular Biology and Biotechnology, Glick and Thompson, Eds., 1993, pp. 67-88.
Moloney, et al., "High efficiency transformation of Brassica napus usingAgrobacterium vectors," Plant Cell Reports, vol. 8, Apr. 1989, pp. 238-242.
Murai, et al., "Phaseolin Gene from Bean is Expressed After Transfer to Sunflower Via Tumor-Inducing Plasmid Vectors," Science, vol. 222, Issue 4623, Nov. 4, 1983, pp. 476-482.
Nagaraju, et al., "Genetic analysis of traditional and evolved Basmati and non-Basmati rice varieties by using fluorescence-based ISSR-PCR and SSR markers," PNAS, vol. 99, Issue 9, Apr. 16, 2002, pp. 5836-5841.
Odell, et al., "Identification of DNA sequences required for activity of the cauliflower mosaic virus 35S promoter," Nature, vol. 313, Feb. 28, 1985, pp. 810-812.
Pan, et al., "Map-based cloning of a novel rice cytochrome P450 gene CYP81A6 that confers resistance to two different classes of herbicides," Plant Molecular Biology, vol. 61, Issue 6, Aug. 2006, pp. 933-943.
Paul, et al., "The isolation and characterisation of the tapetum-specific Arabidopsis thaliana A9 gene," Plant Molecular Biology, vol. 19, Jul. 1992, pp. 611-622.
Phillips, et al., Cell/Tissue Culture and In Vitro Manipulation, Corn and Corn Improvement, vol. 18, Issue 3, Jan. 1988.
Roder, et al., "Efficiency of the tetracycline-dependent gene expression system: complete suppression and efficient induction of the rolB phenotype in transgenic plants," Molecular and General Genetics (MGG), vol. 243, Jan. 1994, pp. 32-38.
Schena et al., "A steroid-inducible gene expression system for plant cells," PNAS, vol. 88, Issue 23, Dec. 1, 1991, pp. 10421-10425.
Sengupta-Gopalan, et al., "Developmentally regulated expression of the bean ß-phaseolin gene in tobacco seed," PNAS, vol. 82, Issue 10, May 1, 1985, pp. 3320-3324.
Shetty, et al., "Stimulation of in vitro shoot organogenesis in Glycine max (Merrill.) by allantoin and amides," Plant Science, vol. 81, Issue 2, 1992, pp. 245-251.
Simpson, et al., "Light-inducible and tissue-specific expression of a chimaeric gene under control of the 5'-flanking sequence of a pea chlorophyll a/b-binding protein gene," EMBO J., vol. 4, Issue 11, Nov. 1985, pp. 2723-2729.
Sprague et al., "Corn and Corn Improvement," American Society of Agronomy, Inc., vol. 18, Third Edition, Jan. 1, 1988.
Steifel, et al., "Expression of a maize cell wall hydroxyproline-rich glycoprotein gene in early leaf and root vascular differentiation," The Plant Cell, vol. 2, Issue 8, Aug. 1990, pp. 785-793.
Stephens, et al., "Agronomic evaluation of tissue-culture-derived soybean plants," Theoretical and Applied Genetics, vol. 82, 1991, pp. 633-635.
Teeri, et al., "Gene fusions to lacZ reveal new expression patterns of chimeric genes in transgenic plants," The EMBO Journal, vol. 8, Issue 2, Feb. 1, 1989, pp. 343-350.
Timko, et al., "Light regulation of plant gene expression by an upstream enhancer-like element," Nature, vol. 318, Dec. 1, 1985, pp. 579-582.
Twell, et al., "Activation and developmental regulation of an Arabidopsis anther-specific promoter in microspores and pollen of Nicotiana tabacum," Sexual Plant Reproduction, vol. 6, Oct. 1993, pp. 217-224.
Twell, et al., "Isolation and expression of an anther-specific gene from tomato," Molecular and General Genetics (MGG), vol. 217, Jun. 1989, pp. 240-245.

(56) References Cited

OTHER PUBLICATIONS

Velten, et al., "Isolation of a dual plant promoter fragment from the Ti plasmid of Agrobacterium tumefaciens," The EMBO Journal, vol. 3, 1984, pp. 2723-2730.
Wan, et al., "Efficient production of doubled haploid plants through colchicine treatment of anther-derived maize callus," Theoretical and Applied Genetics, vol. 77, Issue 6, Jun. 1989, pp. 889-892.
Zhu, et al., "Towards rice genome scanning by map-based AFLP fingerprinting," Molecular and General Genetics (MGG), vol. 261, Issue 1, Feb. 1999, pp. 184-195.
1 Bairu et al, 2011, Plant Growth Regul, 63: 147-173.

\* cited by examiner

INBRED RICE LINE DG263L

1. CROSS REFERENCE TO RELATED APPLICATION

This application claims priority to Provisional Application No. 63/196,202, filed Jun. 2, 2021, which is herein incorporated by reference in the entirety.

2. BACKGROUND

An ancient agricultural crop, rice remains one of the world's principal food crops.

Rice in the United States is classified into three primary market types by grain size, shape, and endosperm composition: long-grain, medium-grain, and short-grain. Typical U.S. long-grain cultivars cook dry and fluffy when steamed or boiled, while medium- and short-grain cultivars cook moist and sticky. Medium grain rice is usually slightly wider than long grain rice and slightly shorter, with a length:width ratio between 2:1 and 3:1.

Rice is a semi-aquatic crop that benefits from flooded soil conditions during part or all of the growing season. In the rice producing regions of the United States, rice is typically grown on flooded soil to optimize grain yields.

Long-grain cultivars have become the principal varieties grown throughout the southern United States.

A goal of rice breeders is to develop stable, high yielding rice cultivars that are agronomically sound. The reasons for this goal are to maximize the amount of grain produced on the land used and to supply food for both animals and humans. To accomplish this goal, the rice breeder must select and develop rice plants that have the traits that result in superior cultivars.

3. SUMMARY

Rice plants and seeds of line DG263L are provided, as are plant parts, tissue cultures of cells, breeding methods, and hybrid rice seed and plants. Inbred rice line designated DG263L is a semi-dwarf, early maturing long grain rice variety (*Oryza sativa* L.).

Inbred line DG263L is described in detail in sections 4.2 and 4.3.

Method of breeding with DG263L, including, e.g., pedigree breeding and hybrid breeding, are detailed in section 4.4.

Tissue cultures of cells from DG263L are described in section 4.5.

The application of molecular biology to DG263L, including transgenes and related methods and gene editing, are described in section 4.6.2.4.6.2.

Industrial uses for DG263L are provided in section 4.7.

4. DETAILED DESCRIPTION

The present disclosure provides a new inbred rice line designated DG263L. Rice plants and seeds of line DG263L are provided, as are plant parts, tissue cultures of cells, breeding methods, and hybrid rice seed and plants.

The seed of inbred rice line DG263L, the plant produced from the inbred rice line DG263L seed, the hybrid rice plant produced from the crossing of the inbred rice line DG263L, and various parts of the inbred rice line DG263L and hybrid rice plants and transgenic versions of the foregoing can be utilized for human food, livestock feed, and as a raw material in industry. DG263L and its hybrids and derived varieties are adapted for growing throughout the rice-growing areas of Texas, Louisiana, Arkansas, Mississippi, Missouri, and Florida, and will also be well suited for growing in many other rice-producing areas throughout the world.

4.1. Definitions

As used herein, the following terms are intended to have the following meanings:

Amylose: Amylose is a type of grain starch that affects cooking behavior. As such, its measured quantity in rice is used to establish cooking properties of Standard US grain classes, or types (long, medium and short grain).

Amylose Percent: "Amylose percent" refers to the percentage of the endosperm starch of milled rice that is amylose. Standard long grains contain 20 to 23 percent amylose. Rexmont-type long grains contain 24 to 25 percent amylose. Short and medium grains contain 14 to 16 percent amylose. Waxy rice contains zero percent amylose. Amylose values, like most characteristics of rice, will vary over environments.

Cell: The term "cell" generally refers to a plant cell, whether isolated, in tissue culture, or included in a plant or plant part.

Chalk: "Chalk" refers to an opaque region of the rice kernel resulting from loose packing of the starch granules. Chalk may occur throughout or in a part of the kernel.

Days to 50% Heading: The term "days to 50% heading" refers to the number of days from emergence to the day when 50% of all panicles are exerted at least partially through the leaf sheath. "Days to 50% heading" is a measure of growth duration.

Essentially all of the physiological and morphological characteristics: The term "essentially all of the physiological and morphological characteristics" refers to a plant having all of the physiological and morphological characteristics of inbred rice line DG263L, except for the characteristics derived from a converted gene.

Gelatinization temperature: "Gelatinization temperature" refers to the temperature at which the consistency of a rice flour-water mixture changes into a jelly. Correlates with the cooking time and texture of a rice product.

Genetically modified: "Genetically modified" refers to an organism that has received genetic material from another, or had its genetic material modified, resulting in a change in one or more of its phenotypic characteristics. Methods used to modify, introduce or delete the genetic material may include mutation breeding, genome editing, backcross conversion, genetic transformation, single and multiple gene conversion, and/or direct gene transfer.

Genome editing: "Genome editing" refers to a type of engineering in which DNA is inserted, replaced, modified, or removed from a plant genome using, e.g., artificially engineered nucleases or other target changes using homologous recombination.

Plant: As used herein, the term "plant" includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like. "Plant" also includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, panicles, glumes, leaves, stems, pistils, anthers and the like. Thus, another aspect of the present disclosure is to provide for cells which upon growth and differentiation produce a cultivar having essentially all of the physiological and morphological characteristics of inbred rice line DG263L. Genetic variants of inbred rice line DG263L can also be obtained as a result of the tissue culture process. Variants recovered by tissue culture of inbred rice line DG263L are another aspect of this invention.

Promoter: As used herein, "promoter" includes reference to a region of DNA upstream from the start of transcription and involved in recognition and binding of RNA polymerase and other proteins to initiate transcription. A plant promoter is a promoter capable of initiating transcription in plant cells, including rice. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

Transgene: "Transgene" refers to a segment of DNA containing a gene sequence that has been isolated from one organism and is introduced into a different organism.

4.2. Variety Description

Inbred rice line designated DG263L is a semi-dwarf, early maturing long grain rice variety (*Oryza sativa* L.). DG263L has a broad germplasm background with excellent yield potential, stable yields across trials, and a strong disease package for the United States market. The line has 26% amylose, with an intermediate gel temperature, low chalk content, and demonstrated good yield and excellent milling attributes in multi-state testing in southern United States rice production areas.

DG263L typically shows 85 days from planting to 50% heading, and is 36 inches in height at maturity.

DG263L was developed from a pedigree selection system at El Campo, TX The line was developed from the cross R9/B1/3/6G4286R//Cypress/Alan. R9, B1, and 6G4286R are all proprietary lines, with 6G4286R acting as a restorer line. Cypress and Alan are US conventional public varieties. Following the cross, plants were selected for strong straw, relatively short height, big panicles, good tillers, high yield potential, good milling and grain quality, and good pollinator ability. From these selections, DG263L was identified. It was entered into the yield trails bulking a F5 row made in El Campo, TX in 2016. DG263L has shown uniformity and stability. The line has been self-pollinated a sufficient number of generations with careful attention to uniformity of plant type and has been increased with continued observation for uniformity.

Inbred rice line DG263L was observed to possess the physiological and morphological characteristics set out in Table 1, based primarily on averages of tests conducted over multiple growing seasons (2017 to 2020) at multiple sites (El Campo, TX; Crowley, LA; Keiser, AR; Clay, AR; Colt, AR; Stuttgart, AR; and Campbell, MO).

TABLE 1

Physiological and Morphological Characteristics of Inbred Rice Line DG263L

Type
Rice Type: Long grain
Maturity
Maturity Days to Heading: 30
Nitrogen Rate (kg/ha): 168
Number of Days: 84
Maturity Class: Very early (85 days or less)
Culm
Culm Angle (degrees from perpendicular after flowering): Erect (less than 30°)
Culm Length or Plant Height (cm): 91.5
Height Class: Short (≤95 cm)
Internode Color after Flowering: Green
Flag Leaf at Maturity
Flag Leaf Width (mm): 15
Flag Leaf Length (cm): 32
Flag Leaf Pubescence: Glabrous
Leaf Angle after Heading: Erect
Flag Leaf Blade Color at Heading: Dark green
Basal Leaf Sheath Color at Heading: Green
Ligule
Ligule Length (mm): 16
Ligule Color: White
Ligule Shape: Acute to acuminate
Collar Color: Green
Auricle Color: Pale green
Panicle
Panicle Length (cm)
Length: 24
High: 26
Low: 22
Panicle Type: Intermediate
Panicle Secondary Branching: Light
Panicle Exsertion Near Maturity: 90-99%
Shattering at Maturity: Low
Threshability: Intermediate
Panicle Habit: Drooping
Grain Spikelet
Awns after Full Heading: Absent
Apiculus Color at Maturity: Straw
Apiculus Color after Full Heading: Straw
Stigma Color: White
Lemma and Palea Color at Maturity: Straw
Lemma and Palea Pubescence: Glabrous
Spikelet Sterility at Maturity: Highly fertile (>90%)
Grain Seed
Seed Coat (Bran) Color: Light brown
Endosperm Type: Nonglutinous (nonwaxy)
Endosperm Translucency: Clear
Endosperm Chalkiness: None
Scent (aroma): Nonscented
Shape Class Ratio
Paddy Shape: Long (3.4:1 and more)
Brown: Long (3.1:1 and more)
Milled: Long (3.0:1 and more)
Measurements of Grain Seed
Paddy
Length (mm): 923
Width (mm): 262
Thickness (mm): 210
L/W Ratio: 3.52
1000 Grains (grams): 24.1
Brown
Length (mm): 665
Width (mm): 225
Thickness (mm): 190
L/W Ratio: 2.95
1000 Grains (grams): 19.6
Milled
Length (mm): 645
Width (mm): 219
Thickness (mm): 171
L/W Ratio: 2.94
1000 Grains (grams): 17.4
Milling Quality (% hulls): 19.5
Milling Yield (% white kernel (head) rice to rough rice): 68.5
% Protein: 7.0

TABLE 1-continued

Physiological and Morphological Characteristics
of Inbred Rice Line DG263L

% Amylose: 26
Alkali Spreading Value: 1.5% KOH to 1.7% KOH
Gelatination Temperature Type: Intermediate
Resistance to Low Temperature
Germination Vigor: High
Spikelet Fertility: High
Seedling Vigor Not Related to Low Temperature
Seedling Vigor: High
Disease Resistance
Narrow Brown Leaf Spot (*Cerospora oryzae*): Resistant
Leaf Smut (*Entyloma oryzae*): Moderately resistant
Brown Leaf Spot (*Helminthosporium oryzae*) (=*Bipolaris oryzae*)
(=*Drechslera oryzae*): Moderately resistant
Straight Head: Moderately resistant
Kernel Smut (*Neovossia horrida*) (=*Tilletia barclayana*): Moderately resistant
Bacterial Blight (*Xanthomonas campestris* pv. *oryzae*): Moderately resistant
Sheath Blight (*Rhizoctonia solani*): Susceptible
Insect Resistance
Rice Water Weevil (*Lissorhoptrus oryzophilus*): Susceptible
Grape colaspis (*Colaspis brunnea*): Susceptible 4.3. Comparisons of Rice Line DG263L with Other Rice Lines Tables 2 to 16 present comparisons of agronomic characteristics and quality ratings of inbred rice line DG263L are to rice lines CL 153, Diamond, and XL 753.

In Table 2, the average main crop yield over two years for inbred rice line DG263L is compared with the yield of rice lines CL 153, Diamond, and XL 753. Yield data was collected in 2017 and 2018 at El Campo, TX

TABLE 2

Average main crop yield (lb/acre) for DG263L, CL 153, Diamond, and XL 753 over two years at El Campo, TX (2017 and 2018)

| Year | Test | DG263L | CL 153 | Diamond | XL 753 |
|---|---|---|---|---|---|
| 2017 | NAS - El Campo, TX | 9098 | 7854 | 8821 | 8965 |
| 2018 | NAS - El Campo, TX | 9229 | 8651 | 9668 | 9911 |
|  | 2017 and 2018 Average | 9163 | 8252 | 9244 | 9438 |

In Table 3, the average main crop yield from a single growing season for inbred rice line DG263L is compared with the yield of rice lines CL 153, Diamond, and XL 753. Yield data was collected in 2019 at El Campo, TX; Crowley, LA; Keiser, AR; Clay, AR; Colt, AR; Stuttgart, AR; and Campbell, MO

TABLE 3

Average main crop yield (lb/acre) for DG263L, CL 153, Diamond, and XL 753 across several trials at multiple locations in Texas, Louisiana, Arkansas, and Missouri (2019)

| Test | DG263L | CL 153 | Diamond | XL 753 |
|---|---|---|---|---|
| NAS - El Campo, TX | 7416 | 6261 | 6703 | 7731 |
| NAS - El Campo, TX | 8820 | 8029 | 8506 | 10112 |
| RRS -Crowley, LA | 9116 | 9379 | 8249 | 12111 |
| NEREC - Keiser, AR | 11475 | 8640 | 8685 | 11025 |
| RRS - Clay, AR | 10710 | 9405 | 10170 | 11520 |
| PTRD - Colt, AR | 9405 | 7560 | 8055 | 9045 |
| RREC - Stuttgart, AR | 11340 | 8460 | 9855 | 11925 |
| RRS - Campbell, MO | 9153 | 7807 | 8865 | 10071 |
| 2019 Grand Average | 9679 | 8192 | 8636 | 10442 |

In Table 4, the average main crop yield from a single growing season for inbred rice line DG263L is compared with the yield of rice lines CL 153, Diamond, and XL 753. Yield data was collected in 2019 at El Campo, TX; Crowley, LA; Palmetto, LA; Arkansas, AR; St. Francis, AR; Mississippi, AR; Desha, AR; Poinsett, AR; Lawrence, AR; Jackson, AR; Jefferson, AR; Greene, AR; Phillips, AR; Lonoke, AR; Clay, AR; Stuttgart, AR; and Campbell, MO

TABLE 4

Average main crop yield (lb/acre) for DG263L, CL 153, Diamond, and XL 753 across several trials at multiple locations in Texas, Louisiana, Arkansas, and Missouri (2020)

| Year | Test | DG263L | CL 153 | Diamond | XL 753 |
|---|---|---|---|---|---|
| 2020 | NAS - El Campo, TX | 10807 | 8596 | 9884 | 11911 |
|  | NAS - El Campo, TX | 9760 | 7374 | 8038 | 10062 |
| 2020 | RSS 1 - Crowley, LA | 11292 | 10878 |  |  |
|  | RSS 2 - Crowley, LA | 11224 | 10585 |  |  |
|  | South Farm - Crowley, LA | 8944 | 8115 |  |  |
|  | Palmetto - LA | 7631 | 7494 |  |  |
|  | EV - LA | 10106 | 9446 |  |  |
|  | RRS - Crowley | 9905 | 10107 |  |  |
|  | RRS - Stuttgart, AR | 10845 | 9180 |  |  |
|  | Arkansas, AR | 9675 |  | 8190 | 9765 |
|  | ST. Francis, AR | 9675 |  | 7695 | 10080 |
|  | Missisippi, AR | 11295 |  | 9945 | 11745 |
|  | Clay, AR | 11745 |  | 10170 | 11340 |
|  | Desha, AR | 10035 |  | 10215 | 11295 |
|  | Poinsett, AR | 11475 |  | 8460 | 11295 |
|  | Lawrence, AR | 11565 |  | 9720 | 12015 |
|  | Jackson, AR | 10530 |  | 9855 | 11745 |
|  | Jefferson, AR | 10845 |  | 10575 | 11340 |
|  | Greene, AR | 8280 |  | 6525 | 5760 |
|  | Phillips, AR | 7560 |  | 9360 | 10665 |
|  | Lonoke, AR | 10755 |  | 8955 | 10755 |
|  | Campbell, MO | 9000 | 7515 | 8280 | 10170 |
|  | Grand Average | 10134 | 8929 | 9058 | 10663 |

Table 5 presents summarized data from Tables 2 to 4, which includes 32 yield trials conducted in multiple sites in Texas, Louisiana, Arkansas, and Missouri from 2017-2020.

TABLE 5

Average main crop yield (lb/acre) for DG263L, CL 153, Diamond, and XL 753 at multiple locations in Texas, Louisiana, Arkansas, and Missouri (2017 to 2020)

| Years | Trials | DG263L | CL 153 | Diamond | XL753 |
|---|---|---|---|---|---|
| 2017-2020 | 32 Yield Trials in TX, LA, AR, and MO | 9960 | 8567 | 8938 | 10494 |

In Table 6, the average days from planting to 50% heading of the main crop for rice line DG263L is compared with that of rice lines CL 153, Diamond, and XL 753. Data was collected from 2017 to 2020 at El Campo, TX and Stuttgart, AR, as indicated.

TABLE 6

Average days from planting to 50% heading of main crop for DGL, CL 153, Diamond, and XL 753 at locations in Texas and Arkansas (2017 to 2020)

| Year | Test | DG263L | CL 153 | Diamond | XL753 |
|---|---|---|---|---|---|
| 2017 | NAS-El Campo, TX | 85 | 86 | 88 | 88 |
| 2018 | NAS- El Campo, TX | 95 | 94 | 95 | 93 |

TABLE 6-continued

Average days from planting to 50% heading of main crop for DGL, CL 153, Diamond, and XL 753 at locations in Texas and Arkansas (2017 to 2020)

| Year | Test | DG263L | CL 153 | Diamond | XL753 |
|---|---|---|---|---|---|
| 2019 | NAS-El Campo, TX | 90 | 90 | 94 | 95 |
|  | NAS-El Campo, TX | 82 | 84 | 86 | 84 |
|  | RREC-Stuttgart, AR | 84 | 86 | 85 | 84 |
| 2020 | NAS-El Campo, TX | 99 | 101 | 103 | 98 |
|  | NAS-El Campo, TX | 85 | 86 | 89 | 84 |
| 2017 to 2020 Grand Average |  | 88 | 90 | 91 | 89 |

In Table 7, the average plant height of the main crop for rice line DG263L is compared with that of rice lines CL 153, Diamond, and XL 753. Data was collected from 2017 to 2020 at El Campo, TX and Crowley, AL, as indicated.

TABLE 7

Average plant height (inches) of the main crop for DGL, CL 153, Diamond, and XL 753 at locations in Texas and Alabama (2017 to 2020)

| Year | Test | DG263L | CL 153 | Diamond | XL753 |
|---|---|---|---|---|---|
| 2017 | NAS-El Campo, TX | 36 | 36 | 40 | 41 |
| 2018 | NAS-El Campo, TX | 39 | 37 | 38 | 40 |
| 2019 | NAS-El Campo, TX | 35 | 34 | 35 | 39 |
|  | NAS-El Campo, TX | 39 | 39 | 38 | 45 |
|  | RRS-Crowley, AL | 41 | 38 | 40 | 40 |
| 2020 | NAS-El Campo, TX | 38 | 38 | 41 | 41 |
|  | NAS-El Campo, TX | 36 | 39 | 38 | 43 |
| 2017 to 2020 Grand Average |  | 37 | 37 | 38 | 41 |

In table 8, whole grain rice milling yield of the main crop for rice line DG263L is compared with that of rice lines CL 153, Diamond, and XL 753. Data was collected from 2017 to 2020 at El Campo, TX; Crowley, AR; Stuttgart, AR; and Campbell MO, as indicated.

TABLE 8

Whole grain rice milling yield (%) of the main crop for DG263L, CL153, Diamond, and XL 753 at multiple locations in Texas, Alabama, Arkansas, and Missouri (2017 to 2020)

| Year | Test | DG263L | CL 153 | Diamond | XL753 |
|---|---|---|---|---|---|
| 2017 | NAS-El Campo, TX | 49 | 51 | 44 | 29 |
| 2018 | NAS-El Campo, TX | 56 | 61 | 59 | 58 |
| 2019 | NAS-El Campo, TX | 55 | 54 | 42 | 20 |
|  | NAS-El Campo, TX | 55 | 59 | 53 | 53 |
|  | RRS-Crowley, AL | 59 | 63 | 59 | 55 |
|  | RREC-Stuttgart, AR | 60 | 63 | 59 | 61 |
|  | RRS-Campbell, MO | 65 | 66 | 63 | 58 |
| 2020 | NAS-El Campo, TX | 55 | 56 | 52 | 49 |
|  | NAS-El Campo, TX | 57 | 59 | 48 | 43 |
| 2017 to 2020 Grand Average |  | 57 | 59 | 53 | 47 |

In table 9, total grain rice milling yield of the main crop for rice line DG263L is compared with that of rice lines CL 153, Diamond, and XL 753. Data was collected from 2017 to 2020 at El Campo, TX; Crowley, AR; Stuttgart, AR; and Campbell MO, as indicated.

TABLE 9

Total grain rice milling yield (%) of the main crop for DG263L, CL153, Diamond, and XL 753 at multiple locations in Texas, Alabama, Arkansas, and Missouri (2017 to 2020)

| Year | Test | DG263L | CL 153 | Diamond | XL753 |
|---|---|---|---|---|---|
| 2017 | NAS-El Campo, TX | 65 | 68 | 67 | 65 |
| 2018 | NAS-El Campo, TX | 67 | 68 | 67 | 67 |
| 2019 | NAS-El Campo, TX | 67 | 66 | 65 | 53 |
|  | NAS-El Campo, TX | 67 | 69 | 67 | 68 |
|  | RRS-Crowley, AL | 69 | 73 | 72 | 73 |
|  | RREC-Stuttgart, AR | 68 | 70 | 69 | 71 |
|  | RRS-Campbell, MO | 73 | 75 | 74 | 75 |
| 2020 | NAS-El Campo, TX | 67 | 70 | 68 | 68 |
|  | NAS-El Campo, TX | 68 | 69 | 67 | 67 |
| 2017 to 2020 Grand Average |  | 68 | 70 | 68 | 67 |

In Tables 10 and 11, seedling vigor of rice line DG263L is compared with that of rice lines CL 153, Diamond, and XL 753. Data was collected in 2017 and 2018 (Table 10), and in 2019 and 2020 (Table 11) at El Campo, TX

TABLE 10

Seedling vigor for DG263L, CL 153, Diamond, and XL 753 across several trails at El Campo, TX (2017 and 2018)*

| Year | Test | DG263L | CL 153 | Diamond | XL 753 |
|---|---|---|---|---|---|
| 2017 | NAS - El Campo, TX | 5 | 5 | 4 | 5 |
| 2018 | NAS - El Campo, TX | 5 | 5 | 4 | 5 |
| 2017 and 2018 Grand Average |  | 5 | 5 | 4 | 5 |

*Plant vigor was taken two weeks after seed emergence based on 1 (very weak) to 5 (very vigor)

TABLE 11

Seedling vigor for DG263L, CL 153, Diamond, and XL 753 across several trails at El Campo, TX (2019 and 2020)*

| Year | Test | DG263L | CL 153 | Diamond | XL 753 |
|---|---|---|---|---|---|
| 2019 | NAS - El Campo, TX | 3.3 | 4.7 | 3.8 | 4.3 |
|  | NAS - El Campo, TX | 5 | 5 | 4 | 5 |

TABLE 11-continued

Seedling vigor for DG263L, CL 153, Diamond, and XL 753 across several trails at El Campo, TX (2019 and 2020)*

| Year | Test | DG263L | CL 153 | Diamond | XL 753 |
|---|---|---|---|---|---|
| 2020 | NAS - El Campo, TX | 4.6 | 4.3 | 4 | 5 |
|  | NAS - El Campo, TX | 5 | 4.6 | 4.6 | 5 |
| 2019 and 2020 Grand Average |  | 4.5 | 4.6 | 4.1 | 4.8 |

*Plant vigor was taken two weeks after seed emergence based on 1 (very weak) to 5 (very vigor)

Tables 12, 13, and 14 present a comparison of the resistance of DG263L, CL 153, Diamond, and XL 753 to sheath blight (*Rhizoctonia solani*), bacterial panicle blight (*Burkholderia glumae*), and rotten neck blast (*Pyricularia oryzae*), respectively.

TABLE 12

Reaction of DG263L, CL 153, Diamond, and XL 753 to sheath blight (*Rhizoctonia solani*) (2019 and 2020)*

| Year | Test | DG263L | CL 153 | Diamond | XL 753 |
|---|---|---|---|---|---|
| 2019 | RRS - Crowley, LA | 7 | 5.3 | 4.4 | 3.8 |
| 2020 | RRS - Crowley, LA | 6.3 | 8 | 5.2 | 4.8 |
| 2019-2020 Grand Average |  | 6.6 | 6.6 | 4.8 | 4.3 |

*Using a scale of 0 = very resistant to 9 = very susceptible

TABLE 13

Reaction of DG263L, CL 153, Diamond, and XL 753 to bacterial panicle blight (*Burkholderia glumae*) (2019 and 2020)*

| Year | Test | DG263L | CL 153 | Diamond | XL 753 |
|---|---|---|---|---|---|
| 2019 | RRS - Crowley, LA | 2.7 | 4.4 | 4.5 | 3.3 |
| 2020 | RRS - Crowley, LA | 2.3 | 4 | 3.6 | 2.7 |
| 2019-2020 Grand Average |  | 2.5 | 4.2 | 4.0 | 3.0 |

*Using s scale of 0 = very resistant to 9 = very susceptible

TABLE 14

Reaction of DG263L, CL 153, Diamond, and XL 753 to rotten neck blast (*Pyricularia oryzae*) (2019 and 2020)*

| Year | Test | DG263L | CL 153 | Diamond | XL 753 |
|---|---|---|---|---|---|
| 2019 | RRS - Crowley, LA | 2.3 | 0.3 | 4.8 | 2.3 |
| 2020 | RRS - Crowley, LA | 1.7 | 0.2 | 2 | 0 |
| 2019-2020 Grand Average |  | 2.0 | 0.2 | 3.4 | 1.2 |

*Using a scale of 0 = very resistant to 9 = very susceptible

In Table 15, rough, brown, and milled grain dimensions, and grain weight from rice line DG263L is compared with that of rice lines CL 153, Diamond, and XL 753. Data was collected from rice grown at El Campo, TX

TABLE 15

Rough, brown, and milled grain dimensions and weight of DG263L, CL 153, Diamond, and XL 753 grown at El Campo, TX (2020)

| Variety | Type | Length mm | Width mm | L/W Ratio | Thickness mm | Weight 1,000 Kernels (g) |
|---|---|---|---|---|---|---|
| DG263L | Rough | 923 | 262 | 3.52 | 210 | 24.1 |
|  | Brown | 665 | 225 | 2.96 | 190 | 19.6 |
|  | Milled | 645 | 219 | 2.94 | 171 | 17.4 |
| CL 153 | Rough | 949 | 254 | 3.73 | 200 | 24.5 |
|  | Brown | 737 | 229 | 3.21 | 177 | 20.1 |
|  | Milled | 679 | 222 | 3.06 | 177 | 17.8 |
| Diamond | Rough | 919 | 251 | 3.66 | 210 | 23.8 |
|  | Brown | 711 | 233 | 3.05 | 188 | 19.4 |
|  | Milled | 678 | 223 | 3.04 | 188 | 16.4 |
| XL 753 | Rough | 943 | 270 | 3.49 | 210 | 26.0 |
|  | Brown | 725 | 239 | 3.03 | 180 | 20.6 |
|  | Milled | 691 | 231 | 2.99 | 170 | 17.8 |

In Table 16, grain amylose content, alkali rating, and gel temperature for grain from rice line DG263L is compared with grain from rice lines CL 153, Diamond, and XL 753.

TABLE 16

Quality rating for DG263L grown at El Campo, TX (2020)

| Year | Variety | Amylose % | Alkali Rating | Gel Temp |
|---|---|---|---|---|
| 2020 | DG263L | 26 | 3.5 | High amylose, intermediate Gel |
|  | CL 153 | 20.1 | 3.8 | Intermediate |
|  | Diamond | 23.4 | 3.5 | Intermediate |
|  | XL 753 | 16.8 | 4.0 | Low amylose, intermediate gel |

4.4. Breeding with Inbred Rice Line DG263L

The present disclosure provides methods for producing a rice plant or seed.

The present disclosure provides methods for producing a rice seed by crossing a first parent rice plant with a second parent rice plant, where the first or the second parent rice plant is a rice plant of inbred rice line DG263L, with the other parent rice plant being of a different rice line. Also provided are methods for producing a rice seed where both the first and the second parent rice plants are rice plants of inbred rice line DG263L. The present disclosure thus provides a multitude of breeding methods involving DG263L, including, for example, selfing, backcrosses, hybrid production, crosses to populations, and the like.

The present disclosure also provides methods for producing a rice plant by crossing a rice plant of line DG263L with a second, different rice plant and growing the resultant progeny seed, and repeating the crossing and growing steps with DG263 progeny plants from 0 to 7 times. All plants produced using inbred rice line DG263L are within the scope of the present disclosure, including those developed from varieties derived from inbred rice line DG263L.

Inbred rice line DG263L can be used in the development of further rice plants. In one embodiment, a method for developing a DG263L-derived progeny rice plant in a rice breeding program includes utilizing a plant of line DG263L or a plant part thereof as a source of breeding material and selecting a progeny plant with morphological and/or physiological characteristics selected from those set out in Tables 1 to 16, and/or selecting a progeny plant with molecular markers in common with inbred rice line DG263L. Breeding methods or steps that can be used in a rice breeding program involving DG263L include pedigree breeding, backcrossing, mutation breeding, and recurrent selection. In addition to these methods, techniques such as RFLP-enhanced selection, genetic marker-enhanced selection (e.g., SSR markers), and the making of double haploids can be used.

Other methods include crossing a plant of inbred line DG263L with a rice plant of a different line, thereby producing a population of rice plants, which, on average, derive 50% of their alleles from rice line DG263L. A plant of the resulting population of rice plants can be selected and repeatedly selfed or sibbed with a rice cultivar resulting from these successive filial generations. The present disclosure thus provides a rice cultivar produced by such a method, where the resulting rice cultivar has obtained at least 50% of its alleles from DG263L.

A person of ordinary skill in the art of rice breeding would know how to evaluate the traits of two rice varieties to determine whether there is any significant difference between the traits express by the two rice varieties. See, for example, Fehr and Walt (1987), Principles of Cultivar Development, pp. 261-286. The present disclosure thus provides DG263L progeny plants comprising a combination of at least two DG263L traits selected from those provided in any of Tables 1 to 16, so that the DG263L progeny rice plant is not significantly different for the selected trait that inbred rice line DG263L. Molecular markers can be used to identify a progeny plant as a DG263 progeny plant. Mean trait values can be used to determine whether trait differences are significant. In some embodiments, the traits are measured on plants grown under the same environmental conditions.

Progeny of DG263L can also be characterized through their filial relationship with inbred rice line DG263L. A breeding cross is a cross made to introduce new genetics into the progeny plants, and is distinguished from a cross such as a self or a sib cross made to select among existing genetic alleles. The lower the number of breeding crosses in the pedigree, the closer the relationship between inbred rice line DG263 and its progeny. Progeny plants produced by the methods described herein can be within 1, 2, 3, 4, or 5 breeding crosses of inbred rice line DG263L.

4.4.1. Pedigree Breeding

Pedigree breeding starts with the crossing of two genotypes, such as inbred rice line DG263L and a rice plant of another line or variety having one or more desirable characteristics that is lacking in, or which complements, inbred rice line DG263L. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: F1 to F2; F2 to F3; F3 to F4; F4 to F5; etc. After sufficient inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. Backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a rice variety may be crossed with another rice variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new rice varieties.

Methods of making a backcross conversion of inbred rice line DG263L are provided. Such methods include the steps of crossing a plant of inbred rice line DG263L with a donor plant comprising a desired trait, selecting an F1 progeny plant comprising the desired trait, and backcrossing the selected F1 progeny plant to a plant of inbred rice line DG263L. Such methods can include the step of obtaining a molecular marker profile of inbred rice line DG263L and using the molecular marker profile to select a progeny plant with the desired trait and the molecular marker profile of inbred rice line DG263L. In one embodiment, the desired trait is a mutant gene or transgene present in the donor parent.

4.4.2. Hybrid Breeding

The inbred rice line DG263L can be used in the production of a first-generation (i.e., $F_1$) hybrid plant. Methods for producing such an $F_1$ hybrid include crossing a first parent rice plant with a second parent rice plant, wherein either the first or the second parent rice plant is a DG263L plant and the other parent rice plant is a different rice plant. Also provided are methods for producing a hybrid rice line derived from DG263L by crossing DG263L with a different rice plant and growing the progeny seed. The crossing and growing steps can be repeated any number of times.

Optionally, either the first or the second parent rice plant can be produced in male-sterile form, using techniques known in the art.

DG263L can be used in both two-line hybrid rice breeding and three-line hybrid rice breeding. Both methods are well known in the art.

4.4.3. Recurrent Selection and Mass Selection

Recurrent selection is a method used in a plant breeding program to improve a population of plants. Inbred rice line DG263L is suitable for use in a recurrent selection program. Recurrent selection involves individual plants cross pollinating with each other to form progeny. The progenies are grown and the superior progeny selected by any number of selection methods, which include individual plant, half-sib progeny, full-sib progeny and selfed progeny. The selected progeny are cross pollinated with each other to form progeny for another population. The resulting population is planted and superior plants are again selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the inter-crossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation.

4.4.4. Mutation Breeding

Mutation breeding can be used to introduce new traits into inbred rice line DG263L. Mutations that occur spontaneously or are artificially induced can be useful sources of variability for a plant breeder. The goal of artificial mutagenesis is to increase the rate of mutation for a desired characteristic. Mutation rates can be increased by many different means including, for example, temperature; long-term seed storage; tissue culture conditions; radiation, such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); or chemical mutagens such as base analogues, (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis, the trait may then be incorporated into existing germplasm by traditional breeding techniques. Mutations created in other rice plants may be used to produce a backcross conversion of inbred rice line DG263L that includes the mutation.

4.4.5. Marker Assisted Breeding

Isozyme Electrophoresis and RFLPs have been widely used to determine genetic composition. See for example, Dinka et al. (2007), Genetics, 176(4):2035-54; Gonzalez et al. (2007) Mol. Plant Microbe Interact. 20(5):534-546; Jin et al. (2006), Plant Mol. Biol. 62(4-5):769-777; Pan et al. (2006), Plant Mol. Biol. 61(6):933-943; and Huang et al. (2007), J. Genet. Genomics, 33(4):330-338.

SSR technology is one of the most efficient and practical marker technologies. More marker loci can be routinely used and more alleles per marker locus can be found using SSRs in comparison to RFLPs. See, e.g., Lawson et al. (2006), Genome Biology, 7:R14; Nagaraju et al. (2002), PNAS USA, 99(9):5836-5841; and Lu et al. (2005), Crop Science. 45:66-76. Single nucleotide polymorphisms (SNPs) may also be used to identify the unique genetic composition of DG263L plants and progeny varieties retaining the unique genetic composition of DG263L. Various molecular marker techniques may be used in combination to enhance overall resolution.

Rice DNA molecular marker linkage maps have been rapidly constructed and widely implemented in genetic studies such as in Zhu et al. (1999), Mol. Gene Genetics, 261(1):184-195; Cheng et al. (2001), Genome Research, 11(12):2133-2141; Ahn et al. (1993), PNAS USA, 90(17): 7980-7984; and Kao et al. (2006), Theor. Appl. Genet. 112(5):891-902. Sequences and PCR conditions of SSR loci in rice as well as the most current genetic map may be found in RiceBLAST and the TIGR Rice Genome Annotation on the world wide web.

One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

4.4.6. Double Haploids

The production of double haploids can also be used for the development of plants with a homozygous phenotype in a breeding program involving DG263L. For example, a rice plant for which inbred rice line DG263L is a parent can be used to produce double haploid plants. Double haploids are produced by the doubling of a set of chromosomes (1 N) from a heterozygous plant to produce a completely homozygous individual. See, e.g., Wan et al. (1989), Theoretical and Applied Genetics, 77:889-892; and U.S. Pat. No. 7,135,615.

4.5. Tissue Culture

Reproduction of inbred rice line DG263L can occur by tissue culture and regeneration. Tissue culture of various tissues of rice and regeneration of plants therefrom is well known in the art, with methods having been widely published. See, e.g., Komatsuda et al. (1991), Crop Sci., 31:333-337; Stephens et al. (1991), Theor. Appl. Genet., 82:633-635; Shetty et al. (1992), Plant Science, 81:245-251; U.S. Pat. Nos. 5,008,200; and 5,024,944. The present disclosure thus provides regenerative cells which, upon growth and differentiation, produce rice plants having the physiological and morphological characteristics of inbred rice line DG263L.

The term "tissue culture" refers to a composition including isolated cells of the same type or cells of different types, or a collection of such cells organized into parts of a plant. Examples of tissue cultures include protoplasts, calli, plant clumps, and plant cells that can generate tissue cultures that form intact plants or parts of plants, such as embryos, pollen, flowers, seeds, glumes, panicles, leaves, stems, roots, root tips, anthers, and the like. Means for preparing and maintaining plant tissue cultures are well known in the art.

4.6. Introduction of a New Trait or Locus into Inbred Rice Line DG263L

Inbred rice line DG263L provides a new genetic line into which a new locus, loci, or trait(s) may be introgressed. Direct transformation and backcrossing are two important methods that can be used to accomplish such an introgression.

4.6.1. Backcross Conversions of Inbred Rice Line DG263L

A backcross conversion of inbred rice line DG263L occurs when DNA sequences are introduced through backcrossing, with inbred rice line DG263L utilized as the recurrent parent. Backcrossing involves the repeated crossing of a DG263L hybrid progeny back to one of the parental rice plants (i.e., the recurrent parent). The recurrent parent can be DG263L, and backcrossing to the recurrent parent can occur 1, 2, 3, 4, 5, 6, 7, 8, 9 or more times.

Both naturally occurring and transgenic DNA sequences can be introduced through backcrossing techniques. In a typical backcross protocol, the original cultivar of interest (recurrent parent) is crossed to a second cultivar (nonrecurrent parent) that carries the single or multiple gene(s) of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single or multiple transferred gene(s) from the nonrecurrent parent.

The selection of a suitable recurrent parent (e.g., DG263L) is an important step for a successful backcrossing procedure. The goal of a backcross protocol is to alter or substitute a single or multiple trait or characteristic in the original line. To accomplish this, a single gene or multiple genes of the recurrent line is/are modified or substituted with the desired gene(s) from the nonrecurrent parent, while retaining essentially all of the rest of the desired genetic (and therefore the desired physiological and morphological) constitution of the recurrent line. The choice of the particular non-recurrent parent will depend on the purpose of the backcross; one of the major purposes is to add some commercially desirable, agronomically important trait to the plant. The exact backcrossing protocol will depend on the characteristic(s) or trait(s) being altered to determine an appropriate testing protocol. Although backcrossing methods are simplified when the characteristic(s) being transferred are the result of the action of a dominant allele(s), a recessive allele may also be transferred. In this instance it may be necessary to introduce a test of the progeny to determine if the desired characteristic(s) has been successfully transferred.

Many single or multiple gene traits have been identified that are not regularly selected for in the development of a new line but that can be improved by backcrossing techniques. Single or multiple gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability, and yield enhancement.

A backcross conversion may produce a plant with a desired trait(s), locus or loci conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. Using marker assisted selection, a backcross conversion can be made in as few as two backcrosses.

The complexity of the backcross conversion method depends on the type of trait being transferred (e.g., single genes or closely linked genes vs. unlinked genes), the level of expression of the trait, the type of inheritance (e.g., cytoplasmic or nuclear) and the types of parents included in the cross. It will be understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance, and herbicide resistance. In addition, an introgression site itself, such as an FRT site, Lox site or other site-specific integration site, may be inserted by backcrossing and utilized for direct insertion of one or more genes of interest into a specific plant variety. In some embodiments, the number of loci that may be backcrossed into inbred rice line DG263L is 1, 2, 3, 4, 5, 6, 7, 8, 9, or 10. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site-specific integration system allows for the integration of multiple genes at the converted loci.

4.6.1.1. Single or Multiple Gene Conversion

A genetic trait which has been engineered into a particular rice hybrid or cultivar using molecular biology techniques can be moved into another hybrid or cultivar using traditional backcrossing techniques. For example, a backcrossing approach can be used to move an engineered trait from a public, non-elite rice plant into an elite rice plant (e.g., DG263L), or from a rice plant containing a foreign gene in its genome into a rice plant which does not contain that gene.

The term "rice plant" also includes any single or multiple gene conversions of that rice plant. The terms single or multiple gene converted plant as used herein refers to those rice plants which are developed by backcrossing.

4.6.2. Molecular Biology

Molecular biology techniques have provided for the isolation and characterization of genetic elements with specific functions, such as encoding specific protein products. DNA sequences, whether from a different species or from the same species which are inserted into the genome via transformation, are referred to herein collectively as "transgenes". In some embodiments, a transgenic variant of inbred rice line DG263L can contain at least one transgene, but can contain at least 1, 2, 3, 4, 5, 6, 7, 8, 9, or 10 transgenes. The present disclosure provides transformed versions of the DG263L inbred line.

Rice is transformable and regenerable such that whole plants containing and expressing desired genes under regulatory control can be produced. General descriptions of plant expression vectors and reporter genes and transformation protocols can be found in the published literature. See, e.g., Gruber et al., "Vectors for Plant Transformation", in Methods in Plant Molecular Biology & Biotechnology, Glich et al., (Eds. pp. 89-119, CRC Press, 1993). Moreover, GUS expression vectors and GUS gene cassettes are available commercially, while luciferase expression vectors and luciferase gene cassettes are also available commercially. General methods of culturing plant tissues are provided, for example, by Maki, et al., "Procedures for Introducing Foreign DNA into Plants" in Methods in Plant Molecular Biology & Biotechnology, Glich et al., (Eds. pp. 67-88 CRC Press, 1993); and by Phillips et al., "Cell-Tissue Culture and In-Vitro Manipulation" in Corn & Corn Improvement, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*. See, e.g., Horsch et al. (1985), Science, 227:1229.

In some embodiments, a process for producing rice plant of line DG263L with a desired trait includes transforming the rice plant with a transgene that confers the desired trait. Another embodiment is the plant produced by this process. The desired trait may be one or more of herbicide resistance; bacterial disease resistance; viral disease resistance; fungal disease resistance; insect resistance; modified fatty acid metabolism; modified carbohydrate metabolism; and male sterility. The specific gene may be any known gene in the art, such as, for example, a polynucleotide conferring resistance to glyphosate; sulfonylurea; imidazolinone; dicamba; glufosinate; phenoxy proprionic acid; L-phosphinothricin; cyclohexane; cyclohexanedione; triazine; 2,4-Dichlorophenoxyacetic acid; hydroxyphenyl-pyruvate dioxygenase (HPPD) inhibitors; and benzonitrile.

A genetic trait which has been engineered into the genome of a particular rice plant can be moved into the genome of another rice plant using traditional breeding techniques (e.g., backcrossing) as described herein.

Plant transformation involves the construction of an expression vector that is functional in plant cells. Such vectors include DNA comprising a gene under control of or operatively linked to a regulatory element (for example, a promoter). The expression vector can contain one or more such operably linked gene/regulatory element combinations. The vector(s) may be in the form of a plasmid and can be used alone or in combination with other plasmids to provide transformed rice plants using transformation methods described below, resulting in the incorporation of transgenes into the genetic material of the rice plant(s).

4.6.2.1. Expression Vectors—Marker Genes

Expression vectors functional in rice plants can include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the art, and include, for example, genes that code for enzymes that metabolically detoxify a selective chemical agent (e.g., an antibiotic or an herbicide), or genes that encode an altered target which is insensitive to the inhibitor. Positive selection methods are also known in the art.

A commonly used selectable marker gene for plant transformation is the neomycin phosphotransferase II (nptII) gene isolated from transposon Tn5, which, when placed under the control of plant regulatory signals, confers resistance to kanamycin. See, e.g., Fraley et al. (1983), PNAS USA, 80:4803. Another commonly used selectable marker gene is the hygromycin phosphotransferase gene, which confers resistance to the antibiotic hygromycin. See, e.g., Vanden Elzen et al. (1985), Plant Mol. Biol., 5:299.

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Other selectable marker genes confer resistance to herbicides such as glyphosate, glufosinate or bromoxynil.

Marker genes for plant transformation not of bacterial origin include, for example, mouse dihydrofolate reductase, plant 5-enol pyruvylshikimate-3-phosphate synthase and plant acetolactate synthase.

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. See, e.g., Jefferson et al. (1987), Plant Mol. Biol. Rep., 5:387; Teeri et al. (1989), EMBO J., 8:343; Koncz et al. (1987), PNAS USA, 84:131; and DeBlock et al. (1984), EMBO J., 3:1681.

A gene encoding Green Fluorescent Protein (GFP) has been utilized as a marker for gene expression in prokaryotic and eukaryotic cells. See, e.g., Chalfie et al. (1994), Science, 263:802. GFP and mutants of GFP can be used as screenable markers.

4.6.2.2. Expression Vectors—Promoters

Genes included in expression vectors functional in rice plants must be driven by a nucleotide sequence comprising a regulatory element such as, for example, a promoter. Several types of promoters are well known in the art, as are other regulatory elements that can be used alone or in combination with promoters.

4.6.2.2.1. Inducible Promoters

An inducible promoter is operably linked to a gene for expression in rice. Optionally, the inducible promoter is operably linked to a nucleotide sequence encoding a signal sequence which is operably linked to a gene for expression in rice. With an inducible promoter, the rate of transcription increases in response to an inducing agent.

Any inducible promoter functional in rice plant cells can be used. Inducible promoters include, but are not limited to, the inducible promoter from the ACEI system, which responds to copper (see, e.g., Meft et al. (1993), PNAS, 90:4567-4571); the In2 gene from maize, which responds to benzenesulfonamide herbicide safeners (see, e.g., Hershey et al. (1991), Mol. Gen Genetics, 227:229-237; and Gatz et al (1994), Mol. Gen. Genetics, 243:32-38); or Tet repressor from Tn10 (see, e.g., Gatz et al. (1991), Mol. Gen. Genetics, 227:229-237).

In some embodiments, an inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (see, e.g., Schena et al. (1991), PNAS USA, 88:0421).

4.6.2.2.2. Constitutive Promoters

A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in accordance with the present disclosure. Constitutive promoters include, but are not limited to, the promoters from plant viruses such as the 35S promoter from CaMV (see, e.g., Odell et al. (1985), Nature, 313:810-812) and the promoters from such genes as rice actin (see, e.g., McElroy et al. (1990), Plant Cell, 2:163-171); ubiquitin (see, e.g., Christensen et al. (1989), Plant Mol. Biol., 12:619-632; and Christensen et al. (1992), Plant Mol. Biol., 18:675-689); pEMU (see, e.g., Last et al. (1991), Theor. Appl. Genet., 81:581-588); MAS (see, e.g., Velten et al. (1984), EMBO J., 3:2723-2730), and maize H3 histone (see, e.g., Lepetit et al. (1992), Mol. Gen. Genetics, 231:276-285; and Atanassova et al. (1992), Plant Journal, 2(3): 291-300).

The ALS promoter, XbaI/NcoI fragment 5' to the Brassica napus ALS3 structural gene (or a nucleotide sequence similarity to said XbaI/NcoI fragment), represents another useful constitutive promoter (see, e.g., PCT application WO 96/30530).

4.6.2.2.3. Tissue-Specific and Tissue-Preferred Promoters

A tissue-specific or tissue-preferred promoter is operably linked to a gene for expression in rice. Optionally, the tissue-specific or tissue-preferred promoter is operably linked to a nucleotide sequence encoding a signal sequence which is operably linked to a gene for expression in rice. Plants transformed with a gene of interest operably linked to a tissue-specific or tissue preferred promoter produce the protein product of the transgene exclusively (tissue-specific) or preferentially (tissue-preferred) in a specific tissue.

Any tissue-specific or tissue-preferred promoter functional in rice plant cells can be utilized in accordance with the present disclosure. Tissue-specific or tissue-preferred promoters include, but are not limited to, a root-preferred promoter, such as that from the phaseolin gene (see, e.g., Murai et al. (1983), Science, 23:476-482; and Sengupta-Gopalan et al. (1985), PNAS USA, 82:3320-3324); a leaf-specific and light-induced promoter such as that from cab or rubisco (see, e.g., Simpson et al. (1985), EMBO J., 4(11): 2723-2729; and Timko et al. (1985), Nature, 318:579-582); an anther-specific promoter such as that from LAT52 (see, e.g., Twell et al. (1989), Mol. Gen. Genetics, 217:240-245); a pollen-specific promoter such as that from Zm13 (see, e.g., Guerrero et al. (1993), Mol. Gen. Genetics, 244:161-168); or a microspore-preferred promoter such as that from apg (see, e.g., Twell et al. (1993), Sex. Plant Reprod., 6:217-224).

4.6.2.3. Signal Sequences

Transport of a protein produced by transgenes to a sub-cellular compartment such as the chloroplast, vacuole, peroxisome, glyoxysome, cell wall or mitochondrion, or for secretion into the apoplast is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or sub-cellular compartment, or for secretion to the apoplast. Many signal sequences are known in the art. See, e.g., Becker et al. (1992), Plant Mol. Biol., 20:49; Knox et al. (1987), Plant Mol. Biol., 9:3-17; Lerner et al. (1989), Plant Physiol., 91:124-129; Fontes et al. (1991), Plant Cell, 3:483-496; Matsuoka et al. (1991), PNAS, 88:834; Gould et al. (1989), J. Cell. Biol., 108:1657; Creissen et al. (1991), Plant J. 2:129; Kalderon et al. (1984), Cell, 39:499-509; Steifel et al. (1990), Plant Cell, 2:785-793.

4.6.2.4. Foreign Proteins Genes and Agronomic Genes

Techniques for the selection and propagation of transformed rice plants, which are well understood in the art, yield a plurality of transgenic plants which are harvested in a conventional manner. For the relatively small number of transgenic plants that show higher levels of expression, a genetic map can be generated, primarily via conventional RFLP, PCR and SSR analysis, which identifies the approximate chromosomal location of the integrated DNA molecule.

Map information concerning chromosomal location is useful for proprietary protection of a subject transgenic plant. If unauthorized propagation is undertaken and crosses made with other germplasm, the map of the integration region can be compared to similar maps for suspect plants to determine if the suspect plants have a common parentage with the subject plant. Map comparisons can involve hybridizations, RFLP, PCR, SSR and sequencing, each of which are conventional and well known in the art.

Through the transformation of rice, the expression of genes can be altered to enhance, confer, or otherwise alter herbicide resistance; bacterial disease resistance; viral disease resistance; fungal disease resistance; insect resistance; modified fatty acid metabolism; modified carbohydrate metabolism; and other triates. Transformation can also be used to insert DNA sequences which control or help control male-sterility. DNA sequences native to rice as well as non-native DNA sequences can be transformed into rice and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs. Knock-outs can be generated by, for example, insertion of a transposable element such as mu or other genetic elements such as a FRT, Lox or other site specific integration site; antisense technology; co-suppression; RNA interference; virus-induced gene silencing; target-RNA-specific ribozymes; hairpin structures; MicroRNA; ribozymes; oligonucleotide-mediated targeted; zinc-finger nuclease-based gene editing; CRISPR/Cas-based gene editing; TALEN-based gene editing; EMN-base gene editing; and other methods or combinations of the above methods known to those of skill in the art.

Agronomic genes can be expressed in transformed plants. More particularly, plants can be genetically engineered to express various phenotypes of agronomic interest. Exemplary genes implicated in this regard include, but are not limited to, those described below.

4.6.2.4.1. Pest and Disease Resistance Genes

Genes that confer to resistance to pests or disease include:
a) Plant resistance genes. Plant defenses are often activated by specific interaction between the product of a disease resistance gene (R) in the plant and the product of a corresponding avirulence (Avr) gene in the pathogen. A rice plant can be transformed with a cloned resistance gene to engineer plants that are resistant to specific pathogen strains.
b) Genes encoding a *Bacillus thuringiensis* protein, a derivative thereof or a synthetic polypeptide modeled thereon.
c) Genes encoding a lectin (e.g., *Clivia miniata* mannose-binding lectin genes).
d) Genes encoding a vitamin binding protein such as avidin.
e) Genes encoding an enzyme inhibitor, such as a protease or proteinase inhibitor or an amylase inhibitor.
f) Genes encoding an insect-specific hormone or pheromone such as an ecdysteroid and juvenile hormone, a variant thereof, a mimetic based thereon, or an antagonist or agonist thereof.
g) Genes encoding an insect-specific peptide or neuropeptide which, upon expression, disrupts the physiology of the affected pest.
h) Genes encoding an insect-specific venom produced in nature by a snake, a wasp, etc. (e.g., scorpion insectotoxic peptide).
i) Genes encoding an enzyme responsible for a hyperaccumulation of a monoterpene, sesquiterpene, steroid, a hydroxamic acid, a phenylpropanoid derivative or another non-protein molecule with insecticidal activity.
j) Genes encoding n enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic.
k) Genes encoding a molecule that stimulates signal transduction (e.g., nucleotide sequences for mung bean calmodulin cDNA clones.
l) Genes encoding a hydrophobic moment peptide.
m) Genes encoding a membrane permease, a channel former or a channel blocker.
n) Genes encoding a viral-invasive protein or a complex toxin derived therefrom. For example, coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.
o) Genes encoding an insect-specific antibody or an immunotoxin derived therefrom. Thus, an antibody targeted to a critical metabolic function in the insect gut would inactivate an affected enzyme, killing the insect.
p) Genes encoding a virus-specific antibody.
q) Genes encoding a developmental-arrestive protein produced in nature by a pathogen or a parasite.
r) Genes encoding a developmental-arrestive protein produced in nature by a plant.
s) Genes involved in the Systemic Acquired Resistance (SAR) Response and/or the pathogenesis-related genes.
t) Antifungal genes.
u) Detoxification genes, such as for fumonisin, beauvericin, moniliformin and zearalenone and their structurally related derivatives.
v) Genes encoding cystatin and cysteine proteinase inhibitors.
w) Defensin genes.

4.6.2.4.2. Herbicide Resistance

Genes that confer herbicide resistance or tolerance are known in the art, and can confer resistance or tolerance to, for example, glyphosate; sulfonylurea; imidazolinone; dicamba; glufosinate; phenoxy proprionic acid; L-phosphinothricin; cyclohexane; cyclohexanedione; triazine; 2,4-Dichlorophenoxyacetic acid; hydroxyphenyl-pyruvate dioxygenase (HPPD) inhibitors; and benzonitrile. Specific examples include:
a) Genes encoding mutant ALS or AHAS enzymes, resulting in resistance to herbicide that inhibits the growing point or meristem, such as an imidazolinone or a sulfonylurea.
b) Mutant 5-enolpyruvlshikimate-3-phosphate synthase (EPSP) and aroA genes, which confer resistance to glyphosate. Glyphosate resistance is also imparted to plants that express a gene that encodes a glyphosate oxido-reductase enzyme as described in U.S. Pat. Nos. 5,776,760 and 5,463,175. In addition, glyphosate resistance can be imparted to plants by the over expression of genes encoding glyphosate N-acetyltransferase. See, e.g., U.S. Pat. No. 7,462,481. A DNA molecule encoding a mutant aroA gene can be obtained under ATCC accession number 39256, and the nucleotide sequence of the mutant gene is disclosed in U.S. Pat. No. 4,769,061.
c) Phosphinothricin acetyl transferase (PAT) and Streptomyces hygroscopicus PAT bar genes confer resistance to other phosphono compounds such as glufosinate.
d) ACCase inhibitor-encoding genes confer resistance to pyridinoxy or phenoxy propionic acids and cyclohexanediones.
e) psbA, gs+, and nitrilase genes confer resistance to herbicides that inhibits photosynthesis, such as a triazine (psbA and gs+ genes) or a benzonitrile (nitrilase gene).

4.6.2.4.3. Value-Added Traits

Value-added traits include:
a) Modified fatty acid metabolism, effected by transforming a plant with an antisense gene of stearyl-ACP desaturase to increase stearic acid content of the plant.
b) Decreased phytate content, effected by: i) introduction of a phytase-encoding gene to enhance breakdown of phytate, adding more free phosphate to the transformed plant; or 2) up-regulation of a gene that reduces phytate content.
c) Modified carbohydrate composition effected, for example, by transforming plants with a gene coding for an enzyme that alters the branching pattern of starch or a gene altering thioredoxin such as NTR and/or TRX and/or a gamma zein knock out or mutant such as cs27 or TUSC27 or en27. Fatty acid metabolism modification genes can also be used to affect starch content and/or composition through the interrelationship of the starch and oil pathways.
d) Altering conjugated linolenic or linoleic acid content by, for example, altering expression of LEC1, AGP, Dek1, Superal1, mi1ps, and various Ipa genes such as Ipa1, Ipa3, hpt or hggt.
e) Altered antioxidant content or composition, such as alteration of tocopherol or tocotrienols by, for example, alteration of a phytl prenyl transferase (ppt) or through alteration of a homogentisate geranyl transferase (hggt).

4.6.2.4.4. Male Sterility

There are several methods available for conferring genetic male sterility, such as multiple mutant genes at separate locations within the genome that confer male sterility, as disclosed in U.S. Pat. Nos. 4,654,465 and 4,727,219, and chromosomal translocations as described in U.S. Pat. Nos. 3,861,709 and 3,710,511. In addition to these methods, U.S. Pat. No. 5,432,068 describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that, confers male fertility to be transcribed.

A tapetum-specific gene, RTS (a rice anther-specific gene) is required for male fertility and its promoter sequence directs tissue-specific gene expression in different plant species. See, e.g., Luo et al. (2006), Plant Molecular Biology, 62(3):397-408. Male sterility can also be controlled by the introduction of a deacetylase gene under the control of a tapetum-specific promoter and with the application of the chemical N-Ac-PPT. See, e.g., WO 01/29237.

Introduction of various stamen-specific promoters can also control male sterility. Rice anther-specific promoters are of particular utility in the production of transgenic male-sterile, monocots and plants for restoring their fertility. See, e.g., U.S. Pat. No. 5,639,948, WO 92/13956, and WO 92/13957.

Male sterility can also be controlled by introducing the barnase and the barstar genes. See, e.g., Paul et al. (1992), Pant Mol. Biol, 19:611-622.

4.6.2.4.5. Site-Specific DNA Integration

Creation of a site for site-specific DNA integration can be achieved by the introduction of FRT sites that may be used in the FLP/FRT system and/or Lox sites that may be used in the Cre/Loxp system. See, e.g., Lyznik et al. (2003), Plant Cell Rep, 21:925-932 and WO 99/25821. Other systems that can be used include the Gin recombinase of phage Mu, the Pin recombinase of *E. coli*, and the R/RS system of the pSR1 plasmid.

4.6.2.4.6. Abiotic Stress Resistance

Genes that affect abiotic stress resistance (including but not limited to flowering, panicle/glume and seed development, enhancement of nitrogen utilization efficiency, altered nitrogen responsiveness, drought resistance or tolerance, cold resistance or tolerance, and salt resistance or tolerance) and increased yield under stress provide a considerable value-add. Many of such genes are known in the art (e.g., OsMAPK5 (positively regulate drought, salt, and cold tolerance and negatively modulate PR gene expression and broad-spectrum disease resistance in rice); rice GF14 genes GF14b, GF14c, GF14e and Gf14f (differentially regulated by salinity, drought, wounding and abscisic acid); CBF genes (mitigates the negative effects of freezing, high salinity, and drought on plants)). For plant transcription factors or transcriptional regulators of abiotic stress, see, e.g. U.S. Publication Nos. 2004/0098764 and 2004/0078852.

Other genes and transcription factors that affect plant growth and agronomic traits such as yield, flowering, plant growth and/or plant structure, can be introduced or introgressed into plants. Many of such genes and transcription factors are known in the art (e.g., LHY, ESD4, CON, VRN1, VRN2, GI, FRI, D8, Rht, TFL, FT, and GAI).

4.6.2.5. Transformation Methods

Numerous methods for plant transformation have been developed, including biological and physical plant transformation protocols. See, e.g., Miki et al., "Procedures for Introducing Foreign DNA into Plants" in Methods in Plant Molecular Biology and Biotechnology, Glick and Thompson, Eds. (CRC Press, Inc., Boca Raton, 1993), pp. 67-88. In addition, expression vectors and in vitro culture methods for plant cell or tissue transformation and regeneration of plants are available. See, e.g., Gruber et al., "Vectors for Plant Transformation" in Methods in Plant Molecular Biology and Biotechnology, Glick and Thompson, Eds. (CRC Press, Inc., Boca Raton, 1993), pp. 89-119.

One method for introducing an expression vector into plants is based on the natural transformation system of *Agrobacterium*. See, e.g., Horsch et al. (1985), Science, 227:1229. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, e.g., Kado (1991), Crit. Rev. Plant Sci., 10:1. Descriptions of *Agrobacterium* vector systems and methods for *Agrobacterium*-mediated gene transfer are provided by Gruber et al., supra, Miki et al., supra, and Moloney et al. (1989), Plant Cell Reports, 8:238. See also, U.S. Pat. No. 5,591,616.

Despite the fact the host range for *Agrobacterium*-mediated transformation is broad, some major cereal crop species and gymnosperms have generally been recalcitrant to this mode of gene transfer, even though some success has recently been achieved in rice and corn. Several methods of plant transformation collectively referred to as direct gene transfer have been developed as an alternative to *Agrobacterium*-mediated transformation.

A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s, sufficient to penetrate plant cell walls and membranes.

Another method for physical delivery of DNA to plants is sonication of target cells. Additionally, liposome and spheroplast fusion have been used to introduce expression vectors into plants. Direct uptake of DNA into protoplasts using $CaCl_2$ precipitation, polyvinyl alcohol or poly-L-ornithine has also been reported. Electroporation of protoplasts and whole cells and tissues have also been described.

Following transformation of rice target tissues, expression of the above-described selectable marker genes can provide for preferential selection of transformed cells, tissues and/or plants, using regeneration and selection methods now well known in the art.

4.6.2.6. Gene Editing

Targeted gene editing resulting in gene knock-out, knock-in, down regulation, or altered function can be conducted on inbred rice line DG263L or a parent plant to be crossed with DG263L. The genome of a rice plant can be edited to modify traits and confer or alter resistances or tolerances to pests, viruses, and herbicides. Several gene editing methodologies are well known in the art, including the clustered regularly interspaced short palindromic repeat (CRISPR)/CRISPR-associate protein system, the transcription activator-like effector nuclease (TALEN) system, the zinc-finger nuclease (ZFN) system, and the engineered homing endonuclease/meganuclease (EMN) system.

4.6.3. Genetic Marker Mapping

In addition to phenotypic observations, a plant can also be identified by its genotype. The genotype of a plant can be characterized through a genetic marker profile which can identify plants of the same variety or a related variety, or be used to determine or validate a pedigree. Genetic marker profiles can be obtained by techniques known in the art, such as isozyme electrophoresis, restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) (which are also referred to as Microsatellites), and single nucleotide polymorphisms (SNPs).

Particular markers used for these purposes are not limited to any particular set of markers, but are envisioned to include any type of marker and marker profile which provides a means of distinguishing varieties.

Primers and PCR protocols for assaying these and other markers are widely known in the art. In addition to being used for identification of inbred rice line DG263L and plant parts and plant cells of inbred rice line DG263L, the genetic profile may be used to identify a rice plant produced through the use of inbred rice line DG263L or to verify a pedigree for progeny plants produced through the use of inbred rice line DG263L. The genetic marker profile is also useful in breeding and developing backcross conversions.

An inbred rice line plant characterized by molecular and physiological data obtained from DG263L is contemplated.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing hybrids or varieties it is preferable if all SSR profiles are performed in the same lab.

Plants and plant parts substantially benefiting from the use of inbred rice line DG263L in their development, such as inbred rice line DG263L comprising a backcross conversion, transgene, or genetic sterility factor, may be identified by having a molecular marker profile with a high percent identity to inbred rice line DG263L. Such a percent identity might be 95%, 96%, 97%, 98%, 99%, 99.5% or 99.9% identical to inbred rice line DG263L.

The SSR profile of inbred rice line DG263L also can be used to identify essentially derived varieties and other progeny varieties developed from the use of inbred rice line DG263L, as well as cells and other plant parts thereof. Progeny plants and plant parts produced using inbred rice line DG263L can be identified by having a molecular marker profile of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% identical to DG263L. Such progeny may be further characterized as being within a pedigree distance of inbred rice line DG263L, such as within 1, 2, 3, 4, or 5 or fewer cross-pollinations to a rice plant other than inbred rice line DG263L or a plant that has inbred rice line DG263L as a progenitor. Unique molecular profiles may be identified with other molecular tools such as SNPs and RFLPs.

While determining the SSR genetic marker profile of the plants described, several unique SSR profiles may also be identified which did not appear in either parent of such rice plant. Such unique SSR profiles may arise during the breeding process from recombination or mutation. A combination of several unique alleles provides a means of identifying a plant variety, an F1 progeny produced from such variety, and progeny produced from such rice plan.

4.7. Industrial Uses

The seed of inbred rice line DG263L, the plant produced from the seed, the hybrid rice plant produced from the crossing of the variety with any other rice plant, hybrid seed, and various parts of the hybrid rice plant can be utilized for human food, livestock feed, and as a raw material in industry. The rice seeds produced by inbred rice line DG263L can be crushed, or a component of the rice seeds can be extracted, in order to comprise a commodity plant product, such as protein concentrate, protein isolate, meal, flour, starch, extract, or oil for a food or feed product.

Rice is can be used as a food source for both animals and humans. Rice and rice byproducts (rice bran, cracked rice) are used as a food for livestock, including cattle and other ruminants.

Inbred rice line DG263L can be used to produce rice meal. Following milling of rice harvested from inbred rice line DG263L, the remaining material or "meal" is collected. The meal includes rice bran, polishings, and some rice flour. Rice meal is primarily used as a feedstuff for livestock.

Inbred rice line DG263L can be used to produce rice flour.

For human consumption, inbred rice line DG263L can be used to produce cooking rice, or other product such as rice flour (used to make, e.g., noodles, rice paper, cake, and dumplings), alcoholic beverages, rice vinegar, rice milk, rice syrup, puffed rice, rice crackers, and rice starch.

Inbred rice line DG263L can further be processed to produce films, packaging, and nutraceutical products.

5. DEPOSIT INFORMATION

Applicant made a deposit of the required number of seeds of Inbred Rice Line DG263L with the National Laboratory for Genetic Resources Preservation (NLGRP), 1111 S Mason St., Fort Collins, CO 80521-4500 and was assigned plant identification number PI 695413. The seeds deposited with the NLGRP on Dec. 17, 2020 were taken from the deposit maintained by Loveland Products, Inc. at LPI Rice Breeding Station in El Campo, TX since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 CFR § 1.808. This deposit of the Inbred Rice Line DG263L will be maintained in the NLGRP depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 CFR §§ 1.801-1.809, including providing an indication of the viability of the sample upon deposit.

6. SPECIFIC EMBODIMENTS

The present disclosure is exemplified by the specific embodiments below.

1. A seed of inbred rice line designated DG263L, wherein a representative sample of seed of DG263L is being stored and maintained by Loveland Products, Inc. at LPI Rice Breeding Station in El Campo, TX, with a representative sample of seed of DG263L to be deposited with the National Laboratory for Genetic Resources Preservation (NLGRP) in accordance with 37 CFR §§ 1.801 to 1.809.

2. A rice plant or a plant part thereof, produced by growing the rice seed of embodiment 1.

3. A rice plant, or a plant part thereof, having essentially all of the physiological and morphological characteristics of inbred rice line designated DGL263L, wherein a representative sample of seed of DG263L is being stored by Loveland Products, Inc. at LPI Rice Breeding Station in El Campo, TX, with a representative sample of seed of DG263L to be deposited with the National Laboratory for Genetic Resources Preservation (NLGRP) in accordance with 37 CFR §§ 1.801 to 1.809.

4. A method comprising growing a plurality of rice seed of embodiment 1.

5. A method comprising growing a plurality of rice seed of embodiment 1 and harvesting seed from a resulting rice plant.

6. A rice seed produced by the method of embodiment 5.

7. A tissue culture of cells produced from the rice plant of embodiment 2.

8. The tissue culture of embodiment 7, wherein said cells are produced from pollen of the rice plant of the rice plant of embodiment 2.

9. The tissue culture of embodiment 7, wherein said cells are produced from an embryo of the rice plant of the rice plant of embodiment 2.

10. The tissue culture of embodiment 7, wherein said cells are produced from a cotyledon of the rice plant of the rice plant of embodiment 2.

11. The tissue culture of embodiment 7, wherein said cells are produced from a hypocotyl of the rice plant of the rice plant of embodiment 2.

12. The tissue culture of embodiment 7, wherein said cells are produced from meristematic cells of the rice plant of the rice plant of embodiment 2.

13. The tissue culture of embodiment 7, wherein said cells are produced from a root of the rice plant of the rice plant of embodiment 2.

14 The tissue culture of embodiment 7, wherein said cells are produced from a root tip of the rice plant of the rice plant of embodiment 2.

15. The tissue culture of embodiment 7, wherein said cells are produced from a pistil of the rice plant of the rice plant of embodiment 2.

16. The tissue culture of embodiment 7, wherein said cells are produced from anthers of the rice plant of the rice plant of embodiment 2.

17. The tissue culture of embodiment 7, wherein said cells are produced from a glume of the rice plant of the rice plant of embodiment 2.

18. The tissue culture of embodiment 7, wherein said cells are produced from a panicle of the rice plant of the rice plant of embodiment 2.

19. The tissue culture of embodiment 7, wherein said cells are produced from a flower of the rice plant of the rice plant of embodiment 2.

20. The tissue culture of embodiment 7, wherein said cells are produced from a leaf of the rice plant of the rice plant of embodiment 2.

21. The tissue culture of embodiment 7, wherein said cells are produced from a stem of the rice plant of the rice plant of embodiment 2.

22. A rice plant regenerated from the tissue culture of embodiment 7 or any one of embodiments 8 to 21.

23. A protoplast produced from the plant of embodiment 2.

24. A protoplast produced from the tissue culture of embodiment 7 or any one of embodiments 8 to 21.

25. A rice plant regenerated from the protoplast of embodiment 23 or embodiment 24.

26. The rice plant of embodiment 22 or embodiment 25, wherein the rice plant has essentially all of the physiological and morphological characteristics of inbred rice line designated DGL263L.

27. A method for producing a hybrid rice seed, comprising crossing the rice plant of any one of embodiments 2, 22, and 25 with a rice plant of a different rice line and harvesting resultant rice seed.

28. A hybrid rice seed produced by the method of embodiment 27.

29. A hybrid rice plant or a plant part thereof, produced by growing the seed of embodiment 28.

30. The method of embodiment 27, further comprising:
(a) crossing a rice plant grown from the resultant rice seed and a rice plant of a different line to produce a seed of a progeny rice plant of a subsequent generation;
(b) growing the seed of a progeny rice plant of a subsequent generation of step produced in step (a) and crossing the resultant progeny rice plant of a subsequent generation with itself or a rice plant of a different line to produce seed of a progeny rice plant of a further subsequent generation;
(c) growing the seed of the progeny rice plant of a further subsequent generation produced in step (b); and
(d) interbreeding the progeny rice plant of a further subsequent generation to produce a resultant inbred rice plant.

31. The method of embodiment 30, further comprising crossing the resultant inbred rice plant with a rice plant of a different line and harvesting resultant rice seed.

32. A rice seed produced by the method of embodiment 30 or embodiment 31.

33. A rice plant or a part thereof, produced by growing the rice seed of embodiment 32.

34. A method of introducing one or more desired traits into inbred rice line DG263L, wherein the method comprises:
(a) crossing a rice plant of inbred rice line DG263L with a rice plant of another rice line that comprises the one or more desired traits to produce progeny plants, wherein a representative sample of seed of the inbred rice line DG263L is being stored and maintained by Loveland Products, Inc. at LPI Rice Breeding Station in El Campo, TX, with a representative sample of seed of DG263L to be deposited with the National Laboratory for Genetic Resources Preservation (NLGRP) in accordance with 37 CFR §§ 1.801 to 1.809;
(b) selecting one or more progeny plants that have the one or more desired traits to produce selected progeny plants;
(c) backcrossing the selected progeny plants with rice plants of inbred rice line DG263L;
(d) selecting for backcross progeny plants that have the one or more desired traits; and
(e) repeating steps (c) and (d) one or more times in succession to produce selected second or higher backcross progeny plants that comprise the one or more desired traits and essentially all of they physiological and morphological characteristics of inbred rice line DG263L.

35. The method of embodiment 34, wherein the one or more desired traits is herbicide resistance.

36. The method of embodiment 34 or embodiment 35, wherein the one or more desired traits is bacterial disease resistance.

37. The method of any one embodiments 34 to 36, wherein the one or more desired traits is viral disease resistance.

38. The method of any one embodiments 34 to 37, wherein the one or more desired traits is fungal disease resistance 39. The method of any one embodiments 34 to 38, wherein the one or more desired traits is insect resistance.

40. The method of any one embodiments 34 to 39, wherein the one or more desired traits is modified fatty acid metabolism.

41. The method of any one embodiments 34 to 40, wherein the one or more desired traits is modified carbohydrate metabolism.

42. The method of any one embodiments 34 to 41, wherein the one or more desired traits is male sterility.

43. A rice plant produced by the method of any one of embodiments 34 to 42.

44. A rice seed harvested from the rice plant of embodiment 43, wherein a rice plant grown from the rice seed comprises essentially all of the morphological and physiological characteristics of inbred rice line designated DG263L.

45. A method for producing inbred rice line DG263L seed, comprising crossing a first inbred parent rice plant with a second inbred parent rice plant and harvesting resultant rice seed, wherein both the first and the second inbred parent rice plants are the rice plant of embodiment 2.

46. A method for producing a hybrid rice seed, comprising crossing the rice plant of embodiment 43 with a different rice plant of a different rice line and harvesting resultant rice seed.

47. A hybrid rice seed produced by the method of embodiment 46, wherein a rice plant grown from the hybrid rice seed comprises essentially all of the morphological and physiological characteristics of inbred rice line designated DG263L.

48. A method comprising transforming the rice plant of embodiment 2 with at least one transgene, wherein the at least one transgene confers to the rice plant herbicide resistance.

49. A method comprising transforming the rice plant of embodiment 2 or embodiment 48 with at least one transgene, wherein the at least one transgene confers to the rice plant bacterial disease resistance.

50. A method comprising transforming the rice plant of any one of embodiments 2, 48, and 49 with at least one transgene, wherein the at least one transgene confers to the rice plant viral disease resistance.

51. A method comprising transforming the rice plant of any one of embodiments 2 and 48 to 50 with at least one transgene, wherein the at least one transgene confers to the rice plant fungal disease resistance.

52. A method comprising transforming the rice plant of any one of embodiments 2 and 48 to 51 with at least one transgene, wherein the at least one transgene confers to the rice plant insect resistance.

53. A method comprising transforming the rice plant of any one of embodiments 2 and 48 to 52 with at least one transgene, wherein the at least one transgene confers to the rice plant modified fatty acid metabolism.

54 A method comprising transforming the rice plant of any one of embodiments 2 and 48 to 53 with at least one transgene, wherein the at least one transgene confers to the rice plant modified carbohydrate metabolism.

55 A method comprising transforming the rice plant of any one of embodiments 2 and 48 to 54 with at least one transgene, wherein the at least one transgene confers to the rice plant male sterility.

56. The method of embodiment 48, wherein the at least one transgene confers herbicide resistance to the rice plant.

57. The method of embodiment 56, wherein the at least one transgene confers to the plant resistance to glyphosate.

58. The method of embodiment 56 or embodiment 57, wherein the at least one transgene confers to the plant resistance to sulfonylurea.

59. The method of any one of embodiments 56 to 58, wherein the at least one transgene confers to the plant resistance to imidazolinone.

60. The method of any one of embodiments 56 to 59, wherein the at least one transgene confers to the plant resistance to dicamba.

61. The method of any one of embodiments 56 to 60, wherein the at least one transgene confers to the plant resistance to glufosinate.

62. The method of any one of embodiments 56 to 61, wherein the at least one transgene confers to the plant resistance to phenoxy proprionic acid.

63. The method of any one of embodiments 56 to 62, wherein the at least one transgene confers to the plant resistance to L-phosphinothricin.

64 The method of any one of embodiments 56 to 63, wherein the at least one transgene confers to the plant resistance to cyclohexone.

65. The method of any one of embodiments 56 to 64, wherein the at least one transgene confers to the plant resistance to cyclohexanedione.

66. The method of any one of embodiments 56 to 65, wherein the at least one transgene confers to the plant resistance to triazine.

67. The method of any one of embodiments 56 to 66, wherein the at least one transgene confers to the plant resistance to 2,4-Dichlorophenoxyacetic acid.

68. The method of any one of embodiments 56 to 67, wherein the at least one transgene confers to the plant resistance to a hydroxyphenyl-pyruvate dioxygenase (HPPD) inhibitor.

69. The method of any one of embodiments 56 to 68, wherein the at least one transgene confers to the plant resistance to benzonitrile.

70 The method of any one of embodiments 48 to 69, wherein the at least one transgene confers modified fatty acid or modified carbohydrate metabolism to the rice plant.

71. The method of any one of embodiments 51 to 70, wherein the at least one transgene encodes fructosyltransferase.

72. The method of any one of embodiments 51 to 71, wherein the at least one transgene encodes levansucrase.

73. The method of any one of embodiments 51 to 72, wherein the at least one transgene encodes alpha-amylase.

74. The method of any one of embodiments 51 to 73, wherein the at least one transgene encodes invertase.

75. The method of any one of embodiments 51 to 74, wherein the at least one transgene encodes starch-branching enzyme.

76. A rice plant or a part thereof, produced by the method of any one of embodiments 48 to 75.

77. A method comprising crossing the rice plant of embodiment 2 with either i) a second rice plant of another rice line which includes a transgene or ii) a transformed rice plant of inbred rice line DG263L to produce a progeny plant comprising the transgene, wherein the transgene is operably linked to a regulatory element in the progeny plant and confers one or more desired traits to the rice plant.

78. The method of embodiment 77, wherein the one or more desired traits is herbicide resistance.

79. The method of embodiment 77 or embodiment 78, wherein the one or more desired traits is bacterial disease resistance.

80. The method of any one embodiments 77 to 79, wherein the one or more desired traits is viral disease resistance.

81. The method of any one embodiments 77 to 80, wherein the one or more desired traits is fungal disease resistance 82. The method of any one embodiments 77 to 81, wherein the one or more desired traits is insect resistance.

83. The method of any one embodiments 77 to 82, wherein the one or more desired traits is modified fatty acid metabolism.

84. The method of any one embodiments 77 to 83, wherein the one or more desired traits is modified carbohydrate metabolism.

85. The method of any one embodiments 77 to 84, wherein the one or more desired traits is male sterility.

86. The method of any one of embodiments 78 to 85, wherein the desired trait is resistance to glyphosate.

87. The method of any one of embodiments 78 to 86, wherein the desired trait is resistance to sulfonylurea.

88. The method of any one of embodiments 78 to 87, wherein the desired trait is resistance to imidazolinone.

89. The method of any one of embodiments 78 to 88, wherein the desired trait is resistance to dicamba.

90. The method of any one of embodiments 78 to 89, wherein the desired trait is resistance to glufosinate.

91 The method of any one of embodiments 78 to 90, wherein the desired trait is resistance to phenoxy proprionic acid.

92. The method of any one of embodiments 78 to 91, wherein the desired trait is resistance to L-phosphinothricin.

93. The method of any one of embodiments 78 to 92, wherein the desired trait is resistance to cyclohexone.

94 The method of any one of embodiments 78 to 93, wherein the desired trait is resistance to cyclohexanedione.

95. The method of any one of embodiments 78 to 94, wherein the desired trait is resistance to triazine.

96. The method of any one of embodiments 78 to 95, wherein the desired trait is resistance to 2,4-Dichlorophenoxyacetic acid.

97. The method of any one of embodiments 78 to 96, wherein the desired trait is resistance to a hydroxyphenyl-pyruvate dioxygenase (HPPD) inhibitor.

98. The method of any one of embodiments 78 to 97, wherein the desired trait is resistance to benzonitrile.

99. The method embodiment 77, wherein the transgene confers modified fatty acid or modified carbohydrate metabolism to the progeny plant.

100. The method of embodiment 99, wherein the transgene encodes fructosyltransferase.

101. The method of embodiment 99, wherein the transgene encodes levansucrase.

102. The method of embodiment 99, wherein the transgene encodes alpha-amylase.

103. The method of embodiment 99, wherein the transgene encodes invertase.

104. The method of embodiment 99, wherein the transgene encodes starch-branching enzyme.

105. A rice plant or a part thereof, produce by the method of any one of embodiments 77 to 104.

106. A method of producing a genetically modified rice plant, comprising applying mutation, gene conversion, genome editing, RNA interference, or gene silencing to a rice plant of embodiment 2.

107. A rice plant produced by the method of embodiment 106, wherein the rice plant comprises essentially all of the morphological and physiological characteristics of inbred rice line designated DG263L.

108. A commodity plant product derived or produced from a plant of embodiment 2.

109. The commodity plant product of embodiment 108, wherein the commodity plant product comprises at least one cell of a rice plant of inbred rice line DG263L.

110. The commodity plant product of embodiment 108 or embodiment 109, wherein the commodity plant product is rice.

111. The commodity plant product of embodiment 108 or embodiment 109, wherein the commodity plant product is rice meal.

112. The commodity plant product of embodiment 108 or embodiment 109, wherein the commodity plant product is rice flour.

113. The commodity plant product of embodiment 108 or embodiment 109, wherein the commodity plant product is rice oil.

114. The commodity plant product of embodiment 108 or embodiment 109, wherein the commodity plant product is a film.

115. The commodity plant product of embodiment 108 or embodiment 109, wherein the commodity plant product is a packaging.

116. The commodity plant product of embodiment 108 or embodiment 109, wherein the commodity plant product is a nutraceutical product.

117. A method of producing a commodity plant product, the method comprising collecting a plant part from the rice plant of embodiment 2.

118. The method of embodiment 117 wherein the plant part is seed.

119. The method of embodiment 117 or embodiment 118, further comprising manipulating the plant part to produce the commodity plant product.

120. The method of any one of embodiments 117 to 119, wherein the commodity plant product is rice.

121. The method of any one of embodiments 117 to 119, wherein the commodity plant product is rice meal.

122. The method of any one of embodiments 117 to 119, wherein the commodity plant product is rice flour.

123. The method of any one of embodiments 117 to 119, wherein the commodity plant product is rice oil.

124. The method of any one of embodiments 117 to 119, wherein the commodity plant product is a film.

125. The method of any one of embodiments 117 to 119, wherein the commodity plant product is a packaging.

126. The method of any one of embodiments 117 to 119, wherein the commodity plant product is a nutraceutical product.

127. Pollen or an ovule of the rice plant of any one of claims 2, 3, 22, 25, 26, 29, 33, 43, 76, 105, 107.

What is claimed is:

1. A method of breeding a long grain rice plant with improved natural disease resistance:
    (a) crossing a first rice plant having one or more desired traits with a rice plant of inbred rice line DG263L, wherein a representative sample of seed of the inbred rice line DG263L has been deposited with the National Laboratory for Genetic Resources Preservation (NL-GRP) under number PI 695413;
    (b) selecting one or more progeny plants that have the one or more desired traits of the first rice plant, wherein the desired traits confer improved natural disease resistance;

(c) backcrossing the selected progeny plants with rice plants of inbred rice line DG263L;
(d) selecting for backcross progeny plants that have the one or more desired traits, wherein the desired traits confer improved natural disease resistance; and
(e) repeating steps (c) and (d) one or more times in succession to produce selected second or higher backcross progeny plants that comprise the one or more desired traits and the physiological and morphological characteristics of inbred rice line DG263L, wherein the desired traits confer improved natural disease resistance.

2. A long grain rice plant resulting from the method of claim 1, wherein the long grain rice plant has improved resistance to one or more of the diseases selected from the group consisting of narrow brown leaf spot, leaf smut, brown leaf spot, straight head, kernel smut and bacterial blight than the first rice plant.

3. A rice seed harvested from the rice plant resulting from the method of claim 1, wherein a rice plant grown from the rice seed comprises the morphological and physiological characteristics of inbred rice line designated DG263L.

4. A method for producing a hybrid rice seed, comprising crossing the rice plant of claim 2 with a different rice plant of a different rice line and harvesting resultant rice seed.

5. A hybrid rice seed produced by the method of claim 4, wherein a rice plant grown from the hybrid rice seed comprises the morphological and physiological characteristics of inbred rice line designated DG263L.

6. A method of producing a commodity plant product, the method comprising collecting a plant part from the rice plant of claim 2.

7. The method of claim 6 wherein the plant part is seed.

8. The method of claim 7, further comprising crushing or extracting a component from the seed to produce the commodity plant product.

9. The method of claim 6, wherein the commodity plant product is rice, rice meal, rice flour, rice oil, a film, a packaging, or a nutraceutical product.

* * * * *